United States Patent [19]

Sato et al.

[11] Patent Number: 4,549,034

[45] Date of Patent: Oct. 22, 1985

[54] REFINED ELECTRICAL INSULATING OIL AND OIL-FILLED ELECTRICAL APPLIANCES

[75] Inventors: Atsushi Sato, Tokyo; Keiji Endo, Yokosuka; Shigenobu Kawakami, Ichikawa; Hitoshi Yanagishita; Shozo Hayashi, both of Yokohama, all of Japan

[73] Assignee: Nippon Petrochemicals Company, Limited, Tokyo, Japan

[21] Appl. No.: 588,654

[22] Filed: Mar. 12, 1984

[30] Foreign Application Priority Data

Dec. 30, 1983 [JP] Japan ................................ 58-250736

[51] Int. Cl.$^4$ ............................ H01B 3/22; H01G 4/22
[52] U.S. Cl. ................................ 17/17 LF; 174/25 C; 252/570; 336/94; 361/315; 585/6.3; 585/6.6
[58] Field of Search ................. 585/6.3, 6.6; 252/570; 174/17 LF; 336/94; 361/315

[56] References Cited

U.S. PATENT DOCUMENTS 4,347,169  8/1982  Sato et al. ........................... 252/570

FOREIGN PATENT DOCUMENTS

| 2634436 | 2/1977 | Fed. Rep. of Germany | 585/6.6 |
| 1338528 | 8/1963 | France | 585/6.6 |
| 7586700 | 7/1975 | Japan | 585/6.6 |
| 53-96497 | 8/1978 | Japan | 585/6.3 |

*Primary Examiner*—Paul Lieberman
*Assistant Examiner*—Robert A. Wax
*Attorney, Agent, or Firm*—Scully, Scott, Murphy & Presser

[57] ABSTRACT

A refined electrical insulating oil and oil-filled electrical appliances impregnated therewith. The electrical insulating oil is quite suitable for use in oil-filled electrical appliances in which insulating materials or dielectric materials made of plastics are employed. The electrical insulating oil is prepared by refining a mixture of unsaturated dimers of styrenes and alkylbiphenyls and/or alkylnaphthalenes, using a solid acidic substance.

9 Claims, No Drawings

REFINED ELECTRICAL INSULATING OIL AND OIL-FILLED ELECTRICAL APPLIANCES

BACKGROUND OF THE INVENTION (1) Field of the Invention

This invention relates to a refined electrical insulating oil and oil-filled electrical appliances which is impregnated with the insulating oil.

More particularly, the present invention relates to an electrical insulating oil and oil-filled electrical appliances, which insulating oil is prepared by refining a mixture of unsaturated dimers of styrenes and alkylbiphenyls and/or alkylnaphthalenes. The electrical insulating oil of the invention is quite suitable for use in oil-filled electrical appliances in which insulating materials or dielectric materials made of plastics such as polyolefins are employed.

(2) Description of the Prior Art

Electrical appliances such as oil-filled capacitors, oil-filled power cables and transformers have recently been made to withstand high electric voltages while being small in size. With this tendency, various kinds of plastic films are used together with conventional insulating paper.

In the conventional art, refined mineral oils, polybutenes, alkylbenzenes, polychlorinated biphenyls and the like are used as electrical insulating oils; however, they have several drawbacks. For example, the use of polychlorinated biphenyls was discontinued because it constitutes a public health hazard that is characteristic of halogenated aromatic hydrocarbons. Furthermore, the conventional electrical insulating oils are not satisfactorily compatible with the foregoing plastic materials such as polyolefin films which are recently used in oil-filled electrical appliances.

With the requirements of high-voltage withstanding and size reduction, it is necessary that the electrical insulating oil has a high dielectric breakdown voltage, a low dielectric loss tangent, and good hydrogen gas absorbing capacity.

The hydrogen gas absorbing capacity indicates the stability of the insulating oil against corona discharge (partial discharge) under high electric voltage conditions. The higher the gas-absorbing capacity, the smaller the likelihood of corona discharge, which leads to the advantage of the insulating oil having excellent stability or durability.

Meanwhile, in order to meet the requirement of high-voltage use, plastic films such as polyolefin films, polystyrene films and polyester films are used to replace either partially or completely the conventional insulating paper as insulating materials or dielectric materials for electrical appliances such as oil-filled electric cables and capacitors. In view of their dielectric strength, dielectric loss tangent and dielectric constant, polyolefin films, especially polypropylene and cross-linked polyethylene films, are preferred as the plastic films.

When these polyolefin films are impregnated with insulating oils, some oils cause the films to swell to some extent. If a film becomes swollen, the thickness of the insulating layer increases. As a result, the resistance to the flow of insulating oil increases in electrical cables, and insufficient impregnation with insulating oil occurs in electric capacitors, causing the formation of voids (unimpregnated portions) and the undesirable lowering of the corona discharge voltage.

In connection with the above-mentioned conventional electrical insulating oils, the values of the dielectric breakdown voltages (BDV) and the dielectric loss tangents (tan $\delta$) are satisfactory to a certain extent, but the hydrogen gas absorbing capacity or corona discharge characteristics and the stability of the dimensions of polypropylene films are not satisfactory.

As described above, the conditions that are required of electrical insulating oils became quite severe in recent years. Therefore, trace quantities of impurities such as residual catalyst that comes from preparation process or some other substances contained in electrical insulating oils often have undesirable influences upon the electrical characteristics of the insulating oils. When an electrical appliance is impregnated with an oil containing trace quantity of such impurities, the service life of the appliance is short. Accordingly, it is important that insulating oils are subjected to refining treatment such as clay treatment before impregnation of insulating oils to electrical appliances, in order to remove the impurities by adsorption. However, in the clay treatment, some components of electrical insulating oil such as olefinic compounds are caused to change, which results in that the electrical insulating oil cannot fully exert its desirable properties.

BRIEF SUMMARY OF THE INVENTION

In view of the above-described conventional state of the art, it is the primary object of the present invention to provide a refined electrical insulating oil and oil-filled electrical appliances which are impregnated with the refined insulating oil and are free from the above-described disadvantages in the conventional art.

Another object of the present invention is to provide an electrical insulating oil which has an excellent dielectric constant and other electrical properties, which has a good hydrogen gas absorbing capacity, and which is highly compatible with plastic film insulating materials.

It is a further object of the present invention to provide oil-filled electrical appliances which have excellent corona discharge characteristics, dielectric breakdown voltage and other advantageous electrical characteristics, and have a long service life.

It is still a further object of the invention to provide a refined electrical insulating oil which contains none of trace impurity that produces undesirable effects and effective components of which are not changed in refining treatment, thereby giving desirable electrical characteristics of the electrical insulating oil.

It is a further object of the present invention to provide oil-filled electrical appliances which are impregnated with the above refined electrical insulating oil and which can be used in severe conditions without causing any troubles.

According to the present invention, the electrical insulating oil is prepared by refining a specific mixture with a solid acidic substance. The specific mixture comprises 1 to 70% by weight of at least one bicyclic monoolefin selected from the group consisting of unsaturated dimers or unsaturated codimers of styrenes such as styrene, $\alpha$-methylstyrene and their monomethyl nuclear substituted compounds, and the remainder of alkyl (including cycloalkyl) biphenyl and/or alkyl (including cycloalkyl) naphthalene.

DETAILED DESCRIPTION OF THE INVENTION

The present invention will be described in more detail.

The above-mentioned bicyclic monoolefin is one or a mixture of the members selected from the group consisting of unsaturated dimers or unsaturated codimers of styrenes such as styrene, o-methylstyrene, or their monomethyl nuclear substituted compounds, for example, vinyltoluene and isopropenyltoluene.

These bicyclic monoolefins are represented by the following general formulae (I) to (III):

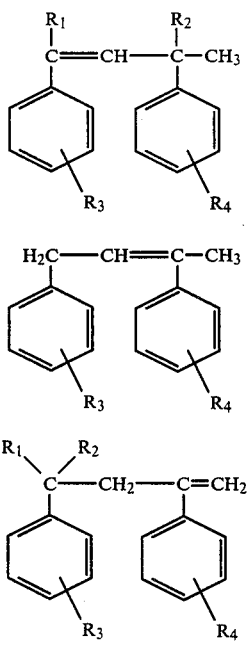

wherein each of $R_1$ to $R_4$ is a hydrogen atom or a methyl group and the total number of carbon atoms in $R_1$ to $R_4$ is an integer from zero to 4.

The compounds represented by the above formulae are exemplified by 1,3-diphenylbutene-1, 1,3-diphenylbutene-2, 1,3-di(methylphenyl)butene-1, 1,3-di(methylphenyl)butene-2, 2,4-diphenyl-4-methylpentene-1, and 2,4-diphenyl-4-methylpentene-2.

The compounds that are used together with the bicyclic monoolefins, are alkylbiphenyl or alkylnaphthalene or their mixture.

The alkyl group in the alkylbiphenyl is exemplified by methyl, ethyl, propyl, isopropyl, n-butyl, sec-butyl, tert-butyl, isobutyl and amyl groups, and cycloalkyl group such as cyclohexyl group. A plurality of the alkyl groups can exist in a compound, however, the total number of carbon atoms in the alkyl groups is preferably in the range of 1 to 10. These alkylbiphenyls can be employed singly or in a mixture of two or more kinds. As preferable components for use in preparing the electrical insulating oil of the invention, the alkylbiphenyls have viscosities of not higher than 30 cSt ($3 \times 10^{-5}$ m$^2$/s) and preferably not higher than 10 cSt ($10^{-5}$ m$^2$/s) at 40° C. One of the most preferable compounds is monoisopropylbiphenyl.

The above alkylbiphenyl can be prepared by high temperature radical reaction of benzene, or by alkylation of benzene with chlorobenzene to obtain biphenyl and further alkylating the biphenyl with an olefin such as ethylene or propylene or with a halogenated hydrocarbon such as chloroethane or chloropropane.

The alkyl group in the other alkylnaphthalene is also exemplified by methyl, ethyl, propyl, isopropyl, n-butyl, sec-butyl, tert-butyl, isobutyl and amyl groups, and cycloalkyl group such as cyclohexyl group. A plurality of the alkyl groups can exist in a compound, however, the total number of carbon atoms in the alkyl groups is preferably in the range of 1 to 10.

These alkylnaphthalenes can be used singly or in a mixture of two or more kinds. As a preferable component of the insulating oil of the invention, the alkylnaphthalene has a viscosity of not higher than 30 cSt ($3 \times 10^{-5}$ m$^2$/s), preferably not higher than 10 cSt ($10 \times 10^{-5}$ m$^2$/s) at 40° C. One of the most preferable compounds is diisopropylnaphthalene.

The alkylnaphthalene can be prepared by the alkylation of naphthalene with propylene, propylchloride or butene.

The quantity of the foregoing bicyclic monoolefin that is mixed with the alkylbiphenyl and/or alkylnaphthalene is in the range of 1 to 70% by weight of the mixture and preferably in the range of 5 to 50% by weight. If the quantity of bicyclic monoolefin is smaller than the above range, even though the refining treatment can be applied, desirable electrical properties owing to the synergistic effect of the combination of the bicyclic monoolefin with the alkylbiphenyl and/or alkylnaphthalene, cannot be produced. On the other hand, when the quantity of the bicyclic monoolefin is larger than the above range, the bicyclic monoolefin is converted into higher boiling components or crystallizable components by the catalytic action during the refining treatment, which makes viscosity and pour point high and which is undesirable. The above obtained mixture has a viscosity of preferably also not higher than 30 cSt ($3 \times 10^{-5}$ m$^2$/s), and more preferably not higher than 10 cSt ($10^{-5}$ m$^2$/s) at 40° C.

As described above, the alkylbiphenyl and/or alkylnaphthalene are mixed with the bicyclic monoolefin. Before the obtained mixture is used for impregnation or else, the mixture is then subjected to refining treatment with using a solid acidic substance in order to eliminate trace quantities of impurities that produce undesirable effects in electrical properties.

The solid acidic substance is a solid substance in the form of powder, particles or the like which are used ordinarily in the refining treatment of electrical insulating oils and which has Bronsted acid points or Lewis acid points. The refining treatment with a liquid acidic substance is not desirable because the liquid acidic substance remaining in the treated oil must be removed after the treatment.

The solid acidic substances are exemplified by acid clay, activated clay that is activated by acid treatment, bentonite, Fuller's earth, silica gel, silica-alumina and activated carbon. Among them, the clay is preferable because it is inexpensive and refining efficiency is high.

The treatment with a solid acidic substance is generally carried out at ordinary temperatures, however, the treatment can also be done at raised temperatures. The time of treatment is not especially restricted and treatment of several minutes to about 1 hour is generally adopted.

After the treatment, the solid acidic substance is removed by, for example, filtration to obtain the electrical insulating oil of the present invention.

Although the alkylbiphenyls and alkylnaphthalenes themselves have excellent electrical properties and good biodegradability, thermal stability and oxidation stability, when they are used in a mixture with the bicyclic monoolefins of the present invention, the hydrogen gas absorbing capacity can be further improved. In addition, in spite of the mixing with the unsaturated compounds of the aromatic olefins, no deterioration in biodegradability, thermal stability and oxidation stability is observed in practical uses, while various electrical properties can be improved.

The electrical insulating oil of the present invention is made of a mixture having the above-described composition; however, the present invention is not restricted to the foregoing composition. That is, in order to improve desired electrical characteristics without impairing the general electrical properties, other conventional electrical insulating oils such as polybutene, mineral oils, alkylbenzenes, diarylalkanes or an aromatic ether such as ditolyl ether can be added to the insulating oil of the present invention in an adequate quantity. When polybutene is added, the volume resistivity and dielectric loss tangent can be improved. The addition of mineral oils can improve the dielectric breakdown voltage, and the addition of alkylbenzenes or other aromatic insulating oils can improve the dielectric breakdown voltage, dielectric loss tangent and pour point.

In order to improve further the oxidation stability, several known antioxidants can be added to the electrical insulating oil of the present invention. As such antioxidants, there are phenol compounds such as 2,6-di-tert-butyl-p-cresol, 2,2'-methylenebis(4-methyl-6-tert-butylphenol), 4,4'-butylidenebis(3-methyl-6-tert-butylphenol), 4,4'-thiobis(3-methyl-6-tert-butylphenol), stearyl-$\beta$-(3,5-di-tert-butyl-4-hydroxyphenol)propionate, tetrakis[methylene-3(3',5'-di-tert-butyl-4'-hydroxyphenyl)propionate]methane, 1,3,5-trimethyl-2,4,6-tris(3,5-di-tert-butyl-4-hydroxybenzyl)benzene, and 1,1,3-tris(2-methyl-4-hydroxy-5-tert-butylphenol)butane; sulfur compounds such as dilauryl thiodipropionate, distearyl thiodipropionate, laurylstearyl thiodipropionate, and dimyristyl thiodipropionate; and phosphorous compounds such as triisodecylphosphite, diphenylisodecylphosphite, triphenylphosphite, and trinonylphenylphosphite.

These antioxidants can be added to the electrical insulating oil singly or in combination of two kinds or more. The addition quantity of the antioxidant is 0.001 to 5% by weight and preferably 0.01 to 2.0% by weight of the electrical insulating oil.

Furthermore, in order to impart a nonflammable property and other desirable effects to the electrical insulating oil of the present invention, several known additives such as phosphoric esters and epoxy compounds can be added to the electrical insulating oil.

The electrical insulating oil of the present invention is good for general uses and, in particular, it is advantageous for the impregnation of oil-filled electrical appliances such as electric capacitors, power cables and transformers.

As described at the beginning of this specification, the requirements of high-voltage withstanding and size reduction of such oil-filled electrical appliances have become severe in recent years. In order to meet these requirements, plastics are used to replace either partially or totally the conventional insulating paper as insulating materials or dielectric materials for the oil-filled electrical appliances. More particularly, as electrical insulating materials (dielectric materials) of electrical capacitors, there is proposed the use of a combination of insulating paper and plastic films such as stretched or nonstretched polypropylene, polymethylpentene, or polyester film; the use of these plastic films singly; the use of embossed or roughened films of these plastic films to facilitate impregnation with the insulating oil; or the use of metallized plastic films, wherein the metallic layer serves as an electrode. Capacitors are made by winding these films together with an electrode material. In the case of oil-filled cables, the electrical insulating materials are made of polyolefin film such as cross-linked or non-cross-linked polyethylene film, stretched or nonstretched polypropylene film, and polymethylpentene film; paper-polyolefin laminated film made by the extrusion of polyolefin onto paper; composite film which is made by cross-linking insulating paper with silane-grafted polyethylene in the presence of a silanol condensation catalyst; or an artificial paper sheet which is made by mixing wood pulp and polyolefin fiber. Cables are made by winding tapes of these films around electric conductors.

The above capacitors and cables are impregnated or filled with the insulating oil of the present invention according to conventional methods.

The electrical insulating oil of the present invention is excellent in compatibility with plastic materials. Accordingly, the electrical insulating oil is quite suitable for use in oil-filled electrical appliances such as electric capacitors and electric cables in which plastic materials are used for either part or all of the insulating material or dielectric material.

More particularly, when an electric capacitor is provided with an insulating (dielectric) material that is partially or totally made of plastics, especially polyolefin, and when it is impregnated with the electrical insulating oil of the present invention, the insulating material can be fully and completely impregnated with the electrical insulating oil because swelling of the insulating material is slight, and voids (unimpregnated portions) are not formed. Accordingly, corona discharge due to the convergence of electric fields to the voids hardly occurs, and dielectric breakdown can be well avoided. Furthermore, the electrical insulating oil of the present invention has excellent hydrogen gas absorbing capacity and corona discharge resistance under high-voltage stress, so that is is possible to obtain both a long service life and high-voltage use of the electrical appliances.

In the case of electric power cables, a change in dimensions of the insulating material due to swelling is small, and resistance to the insulating oil flow can be made low so that oil impregnation can be performed in a short time. Of course, it will be understood that, because of the ease of impregnation, voids are hardly formed and the dielectric breakdown voltage becomes higher. When a cable is made by using an insulating material of a laminated film or composite film made of plastic material and paper, peeling, creasing and buckling of the insulating material upon bending of the cable do not occur even when the insulating material has been in contact with the electrical insulating oil for a long time. Further, as in the case of the electric capacitor, a power cable having a good corona discharge resistance can be obtained due to the excellent hydrogen gas absorbing capacity of the electrical insulating oil. Accordingly, it is also possible to obtain a long service life and high-voltage use, as for the capacitors.

According to the present invention, the above-described advantageous features can be improved by impregnation with the electrical insulating oil consisting of a plurality of specific component materials, owing to the synergistic effect between the component materials. Furthermore, the good electrical characteristics, biodegradability, thermal resistance, and oxidation stability of each component material can be well maintained, and at the same time, the viscosity and pour point of the electrical insulating oil composition can be adjusted within desired ranges. Therefore, the manufacture of oil-filled electrical appliances is facilitated, and oil-filled electrical appliances exhibiting high performance under any use conditions can be obtained.

In the present invention, the electrical insulating oil is free from the adverse effects of trace impurities as the oil has been refined. Accordingly, each component fully exerts its effects and the above-described sinergistic effects can also be produced.

In the following, the electrical insulating oil and electrical appliances impregnated therewith according to the present invention will be described in more detail with reference to several examples.

EXAMPLES AND COMPARATIVE EXAMPLES

(A) Preparation of Electrical Insulating Oils by Mixing and refining

In accordance with the compositions shown in Table 1, various samples of insulating oil mixtures were prepared. To each sample oil was added 1.0 wt. % of activated clay and was stirred for 45 minutes at room temperature, thereby performing refining treatment. After the treatment, the clay was filtered off.

With regard to the sample oils except Examples 1 and 8 (consisting of sole alkylbiphenyl or alkylnaphthalene), the change of bicyclic monoolefins in oil mixtures after clay treatment was examined by gas chromatography. The results of this test are shown in the following Table 2.

TABLE 2

| Example No. | Change of Olefins after Treatment | | | |
|---|---|---|---|---|
| | Unconverted Compounds (%) | Cyclized Saturated Comp. (%) | Heavier Product (%) | Total (%) |
| 2 | 96 | 4 | tr. | 100 |
| 3 | 92 | 8 | tr. | 100 |
| 4 | 7 | 68 | 25 | 100 |
| 5 | 95 | 4 | 1 | 100 |
| 6 | 99 | 1 | tr. | 100 |
| 7 | 56 | 37 | 7 | 100 |
| 9 | 97 | 3 | tr. | 100 |
| 10 | 99 | 1 | tr. | 100 |
| 11 | 5 | 68 | 27 | 100 |

(B) Electrical Characteristics

The electrical characteristics of the sample oils that were refined in the foregoing test, were determined according to JIS C 2101. The results are shown in the following Table 3. Incidentally, the viscosities of all the insulating oils of the present invention were not higher than 10 cSt ($10^{-5}$ m$^2$/s) at 40° C.

TABLE 3

| Test Item | Example No. | | | | | |
|---|---|---|---|---|---|---|
| | 2 | 3 | 5 | 6 | 9 | 10 |
| Dielectric Breakdown Voltage (kV/2.5mm) | >70 | >70 | >70 | >70 | >70 | >70 |
| Dielectric Loss (tan δ) (% at 80° C.) | 0.023 | 0.022 | 0.022 | 0.021 | 0.031 | 0.033 |
| Volume Resistivity (Ω · cm at 80° C.) | $8.0 \times 10^{14}$ | $8.5 \times 10^{14}$ | $8.3 \times 10^{14}$ | $8.6 \times 10^{14}$ | $8.9 \times 10^{14}$ | $8.7 \times 10^{14}$ |
| Dielectric Constant | 2.47 | 2.50 | 2.50 | 2.52 | 2.54 | 2.55 |

(C) Test of Oil-Filled Capacitors

Oil-filled capacitors were made according to the following procedure with using the refined sample oils prepared above. As shown in Table 2, in the oils of Examples 4, 7 and 11, contents of olefins were much reduced by the clay treatment and viscosities of the oils became high by the formation of heavier components. Therefore, these treated oils were not used as they were not suitable for impregnation. Incidentally, 0.2 wt % of BHT was added as an antioxidant to each sample oils.

In connection with the oils in Examples 1 to 3, 5, and 6, two-ply polypropylene films (each 14µ thick) were used as a dielectric material. The dielectric material and aluminum foil as an electrode were wound together according to the conventional method to make model capacitors for impregnation. They were impregnated

TABLE 1

| Example No. | Bicyclic Aromatic Olefin | wt. % | Biphenyl or Naphthalene | wt. % |
|---|---|---|---|---|
| 1 | — | — | Monoisopropylbiphenyl | 100 |
| 2 | 2,4-Diphenyl-4-methylpentene-1 | 10 | " | 90 |
| 3 | " | 40 | " | 60 |
| 4 | " | 80 | " | 20 |
| 5 | 2,4-Diphenyl-4-methylpentene-1 (65%) / 2,4-Diphenyl-4-methylpentene-2 (35%) | 20 | " | 80 |
| 6 | 1,3-Diphenylbutene-1 | 10 | " | 90 |
| 7 | " | 95 | " | 5 |
| 8 | — | — | Diisopropylnaphthalene | 100 |
| 9 | 2,4-Diphenyl-4-methylpentene-1 | 10 | " | 90 |
| 10 | 1,3-Diphenylbutene-1 | 10 | " | 90 |
| 11 | 2,4-Diphenyl-4-methylpentene-1 | 90 | " | 10 | with the oils in vacuum to prepare oil-filled capacitors of about 0.5 μF in electrostatic capacitance.

In connection with the oils in Examples 8, 9 and 10, 28μ thick, 62 mm wide polypropylene film and 12μ thick, also 62 mm wide insulating paper were used and they were put together in layers. As an electrode, 7μ thick, 50 mm wide aluminum foil was used. They were wound together in a usual manner to make model capacitors for oil impregnation. They were impregnated with the respective oils in vacuum to prepare oil-filled capacitors of about 0.8 μF in electrostatic capacitance.

Corona starting voltages (CSV) and corona ending voltages (CEV) were then determined by applying electric voltages to the capacitors thus prepared. The temperature of the test was 30° C. The results of this test are shown in the following Table 4.

Meanwhile, similar oil-filled capacitors were applied with a constant alternating voltage until the capacitors were broken, thereby obtaining breakdown times, which are also shown in Table 4. Each result of breakdown time was calculated such that seven capacitors impregnated with the same oil were tested and the maximum value and minimum value were neglected and the average of the other five breakdown times was adopted as the resultant value. Furthermore, the breakdown times are shown in relative values. That is, in Examples 1 to 3, 5 and 6, the indicated values are relative values to the oil of Example 1 as 1.0. In Examples 8, 9 and 10, the indicated values are relative values to the oil of Example 8 as 1.0.

TABLE 4

| Example No. | CSV (kV) | CEV (kV) | Breakdown Time (Relative Value) |
|---|---|---|---|
| 1 | 2.5 | 2.1 | 1.0 |
| 2 | 2.9 | 2.5 | 8.8 |
| 3 | 3.2 | 2.5 | 12.5 |
| 5 | 3.1 | 2.4 | 9.7 |
| 6 | 3.0 | 2.3 | 3.9 |
| 8 | 1.9 | 1.1 | 1.0 |
| 9 | 2.9 | 1.9 | 4.0 |
| 10 | 2.7 | 1.6 | 2.6 |

What is claimed is:

1. A refined electrical insulating oil which is prepared by refining a mixture using a solid acidic substance, said mixture comprising 1 to 70% by weight of at least one bicyclic monoolefin selected from the group consisting of unsaturated dimers or unsaturated codimers of styrenes such as styrene, α-methylstyrene and their monomethyl nuclear substituted compounds and the remainder of alkyl (including cycloalkyl) biphenyl and/or alkyl (including cycloalkyl) naphthalene.

2. The refined electrical insulating oil in claim 1, wherein said solid acidic substance is clay.

3. The refined electrical insulating oil in claim 1, wherein said bicyclic monoolefin is 2,4-diphenyl-4-methylpentene-1 or 2,4-diphenyl-4-methylpentene-2.

4. An oil-filled electrical appliance which is impregnated with an electrical insulating oil which oil is prepared by refining a mixture using a solid acidic substance, said mixture comprising 1 to 70% by weight of at least one bicyclic monoolefin selected from the group consisting of unsaturated dimers or unsaturated codimers of styrenes such as styrene, α-methylstyrene and their monomethyl nuclear substituted compounds and the remainder of alkyl (including cycloalkyl) biphenyl and/or alkyl (including cycloalkyl) naphthalene.

5. The oil-filled electrical appliance in claim 4, wherein said solid acidic substance is clay.

6. The oil-filled electrical appliance in claim 4, wherein said bicyclic monoolefin is 2,4-diphenyl-4-methylpentene-1 or 2,4-diphenyl-4-methylpentene-2.

7. The oil-filled electrical appliance in claim 4, wherein said oil-filled electrical appliance is one member selected from the group consisting of oil-filled capacitor, oil-filled cable and transformer.

8. The oil-filled electrical appliance in claim 4, wherein the insulating material or dielectric material used in said oil-filled electrical appliance is the material made of insulating paper, plastic film or the combination thereof.

9. The oil-filled electrical appliance in claim 8, wherein said plastic film is polyethylene film or polypropylene film.

* * * * *